(12) United States Patent
Levin

(10) Patent No.: US 7,897,825 B2
(45) Date of Patent: *Mar. 1, 2011

(54) HEAVY AROMATICS PROCESSING CATALYST AND PROCESS OF USING THE SAME

(75) Inventor: Doron Levin, Highland Park, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/640,933

(22) Filed: Dec. 17, 2009

(65) Prior Publication Data

US 2010/0094068 A1    Apr. 15, 2010

Related U.S. Application Data

(63) Continuation of application No. 12/249,279, filed on Oct. 10, 2008, now Pat. No. 7,663,010.

(60) Provisional application No. 60/984,193, filed on Oct. 31, 2007.

(51) Int. Cl.
*C07C 6/12* (2006.01)

(52) U.S. Cl. ........................ 585/319; 585/475

(58) Field of Classification Search ............ 585/319, 585/475

See application file for complete search history.

(56) References Cited

U.S. PATENT DOCUMENTS

| | | |
|---|---|---|
| 5,030,787 A | 7/1991 | Absil et al. |
| 5,905,051 A | 5/1999 | Wu et al. |
| 5,942,651 A | 8/1999 | Beech, Jr. et al. |
| 7,148,391 B1 | 12/2006 | Buchanan et al. |
| 7,419,931 B2 | 9/2008 | Serra et al. |
| 2005/0065017 A1 | 3/2005 | McMinn et al. |
| 2006/0100471 A1 | 5/2006 | Alfaro et al. |

FOREIGN PATENT DOCUMENTS

| | | |
|---|---|---|
| EP | 1 586 376 | 10/2005 |
| EP | 1 655 277 | 5/2006 |
| WO | 00/38834 | 7/2000 |
| WO | 2004/046278 | 6/2004 |

*Primary Examiner*—Thuan Dinh Dang
(74) *Attorney, Agent, or Firm*—Andrew B. Griffis

(57) ABSTRACT

This disclosure relates to a catalyst system adapted for transalkylation a $C_9+$ aromatic feedstock with a $C_6$-$C_7$ aromatic feedstock, comprising: (a) a first catalyst comprising a first molecular sieve having a Constraint Index in the range of 3-12 and 0.01 to 5 wt. % of at least one source of a first metal element of Groups 6-10; and (b) a second catalyst comprising a second molecular sieve having a Constraint Index less than 3 and 0 to 5 wt. % of at least one source of a second metal element of Groups 6-10, wherein the weight ratio of the first catalyst over the second catalyst is in the range of 5:95 to 75:25 and wherein the first catalyst is located in front of the second catalyst when they are brought into contacting with the $C_9+$ aromatic feedstock and the $C_6$-$C_7$ aromatic feedstock in the present of hydrogen.

13 Claims, No Drawings

HEAVY AROMATICS PROCESSING CATALYST AND PROCESS OF USING THE SAME

CROSS REFERENCE TO RELATED APPLICATIONS

This application is a Continuation Application of U.S. application Ser. No. 12/249,279, filed Oct. 10, 2008, now U.S. Pat. No. 7,663,010, which claims the benefit of U.S. Provisional Application No. 60/984,193, filed Oct. 31, 2007, both applications of which are hereby incorporated by reference in their entirety. This application is also related to concurrently filed patent application Ser. No. 12/640,742.

FIELD

The disclosure relates to the catalyst, process and apparatus for conversion of heavy aromatics, specifically C9+ aromatics, to lighter aromatic products, particularly xylenes.

BACKGROUND

A source of benzene and xylene is catalytic reformate, which is prepared by contacting a mixture of petroleum naphtha and hydrogen with a strong hydrogenation/dehydrogenation catalyst, such as platinum, on a moderately acidic support, such as a halogen-treated alumina. Usually, a $C_6$ to $C_8$ fraction is separated from the reformate and extracted with a solvent selective for aromatics or aliphatics to produce a mixture of aromatic compounds that is relatively free of aliphatics. This mixture of aromatic compounds usually contains benzene, toluene and xylenes (BTX), along with ethylbenzene.

Refineries have also focused on the production of benzene and xylene by transalkylation of $C_9+$ aromatics and toluene over noble metal-containing zeolite catalysts. During the transalkylation of $C_9+$ aromatics and toluene to high value petrochemical products, such as benzene and xylene, over catalysts containing noble metals, by-products, such as saturated compounds, are typically produced in the process. These by-products can boil in the same temperature range as the desired aromatic products, making separation of the desired products at high purity levels difficult. For example, a commercial benzene product may need a purity of 99.85 wt. % or higher. However, initial benzene purity after distillation of a transalkylation reaction product is typically only 99.2% to 99.5% due to the presence of coboilers, such as methylcyclopentane, cyclohexane, 2,3-dimethylpentane, dimethylcyclopentane and 3-methylhexane. Therefore, an additional extraction step is usually required to further improve benzene product purity to the desired level.

One solution to the problem of the production of benzene co-boilers during the transalkylation of heavy aromatics is disclosed in U.S. Pat. No. 5,942,651 and involves the steps of contacting a feed comprising $C_9+$ aromatic hydrocarbons and toluene under transalkylation reaction conditions with a first catalyst composition comprising a zeolite having a constraint index ranging from 0.5 to 3, such as ZSM-12, and a hydrogenation component. The effluent resulting from the first contacting step is then contacted with a second catalyst composition which comprises a zeolite having a constraint index ranging from 3 to 12, such as ZSM-5, and which may be in a separate bed or a separate reactor from the first catalyst composition to produce a transalkylation reaction product comprising benzene and xylene. A benzene product having a purity of at least 99.85% may be obtained by distilling the benzene from the transalkylation reaction product, without the need for an additional extraction step. According to the '651 patent, the second catalyst composition comprises up to 20 wt. % of the total weight of the first and second catalyst compositions.

U.S. Pat. No. 5,905,051 discloses a process for converting a hydrocarbon stream such as, for example, a $C_9+$ aromatic compound to $C_6$ to $C_8$ aromatic hydrocarbons, such as xylenes, by contacting the stream with a catalyst system comprising a first catalyst composition and a second catalyst composition, wherein said catalyst compositions are present in separate stages and are not physically mixed or blended and wherein said first catalyst composition is a metal-promoted, alumina- or silica-bound zeolite beta, and said second catalyst composition is ZSM-5 having incorporated therein an activity promoter selected from the group consisting of silicon, phosphorus, sulfur, and combinations thereof. According to the '051 patent, the use of the separate catalytic stages improves the conversion of $C_9+$ aromatic compounds and naphthalenes to xylenes and decreases the amount of undesirable ethylbenzene in the product.

U.S. Pat. No. 5,030,787 discloses an improved disproportionation/transalkylation process. The improved process of this invention is conducted such that transalkylation of a $C_9+$ aromatics feedstock, or disproportionation of a feedstock containing toluene and $C_9+$ aromatic(s), is carried out in the vapor-phase by containing said feedstock in a reaction zone with a catalyst comprising a zeolite possessing a Constraint Index, as defined below, of from 1 to about 3 and preferably which has been hydrogen, hydrogen precursor and/or non-noble Group VIII metal exchanged, thermally treated and/or hydrothermally treated, under conditions effective to convert such feedstock to a product containing substantial quantities of $C_6$-$C_8$ aromatic compounds, e.g. benzene and xylene(s), especially the latter. The product effluent is separated and distilled to remove the desired products. If desired, any unreacted material(s), e.g., toluene and/or $C_9+$ compound(s), can be recycled.

U.S. Pat. No. 5,030,787 discloses a transalkylation process to convert a heavy aromatics feed to lighter aromatics products, such as benzene, toluene and xylenes by contacting a $C_9+$ aromatics fraction and benzene and/or toluene over a catalyst comprising a zeolite, such as ZSM-12, and a hydrogenation component, preferably platinum. The catalyst, with hydrogenation component, is treated to reduce aromatics loss. Treatment includes exposure to steam and/or sulfur after incorporation of the hydrogenation component. For additional stability and aromatics retention, the steamed and/or sulfur treated catalyst is sulfided by cofeeding a source of sulfur. In a further embodiment of the invention, a low hydrogen partial pressure is employed to retain aromatics.

U.S. Pat. No. 7,148,391 discloses a single stage catalyst system comprising at least two different molecular sieves that exhibits enhanced activity for the removal of ethyl -group containing aromatic compounds in $C_9+$ aromatic feeds without overall reduction in the conversion of the $C_9+$ feed to useful compounds, such as xylenes.

Improving catalytic activity and stability are challenges for most of the catalytic transalkylation processes. High activity catalyst normally requires less catalyst and/or less severe reaction conditions to manufacture the same amount of product, which means lower cost for production and high production efficiency. As the catalyst ages with increasing time on stream, higher temperatures are normally required to maintain constant conversion. When the maximum reactor temperature is reached, the catalyst needs to be replaced or regenerated. Depending on the feed composition, the cycle length varies from a few months to as long as a few years for a transalkylation catalyst. A catalyst having high stability normally requires less frequent regeneration or change-out and long time on stream, which translates to lower cost for production and high production efficiency.

The aging rate of catalysts used for the transalkylation of heavy aromatics is normally dependent on the nature of the feed composition. The higher the ratio of $C_9+$ aromatics to $C_6$-$C_7$ aromatics, the greater the aging rate. In addition, the aging rate usually increases with an increasing concentration of material having $C_{10}+$ aromatics, which are by-products of the transalkylation process. There are many chemical reactions that can lead to the formation of these heavier compounds, for example:

Ethyl-methylbenzene+Ethyl-methylbenzene→Toluene+$C_{11}$ (1)

Ethyl-methylbenzene+Ethyl-methylbenzene→Ethylbenezene+$C_{10}$ (2)

Ethyl-methylbenzene+Trimethylbenzene→Toluene+$C_{11}$ (3)

Propylbenzene+Toluene→Benzene+$C_{10}$ (4)

Ethyl-dimethylbenzene+Ethyl-dimethylbenzene→Xylene+$C_{12}$ (5)

Ethyl-dimethylbenzene+Trimethylbenzene→Xylene+$C_{11}$ (6)

There is, therefore, a need for a catalyst system to minimize the formation of these heavy aromatic compounds as they may be precursors for the formation of coke which reduces catalyst activity. One common feature of these reactions producing heavy aromatics is that most of them contain at least one reactant having an alkyl substituent with two or more carbon atoms, for example, an ethyl group or a propyl group. These molecules normally comprise a significant fraction of the feed to a transalkylation unit. Sometimes, ethyl-methylbenzenes and ethyl-dimethylbenzenes can comprise up to one third of the $C_9+$ feed to the transalkylation unit. It has now been discovered that minimizing the reactions of these ethyl and propyl aromatics improves catalytic activity and/or aging rate.

In order to minimize these reactions of $C_{10}+$ formation, it is preferable to dealkylate the ethyl and propyl groups from the aromatic molecules, and saturate the resulting olefin to prevent realkylation onto an aromatic ring. We surprisingly found that by dealkylating the ethyl and/or propyl groups in the feedstock, the formation of heavier aromatics, i.e., $C_{10}+$ aromatics, is minimized, therefore reducing the catalyst aging rate. Not intended to be limited by any theory, we believe that it is desirable to de-alkylate the ethyl and propyl groups in the feed before undergoing transalkylation reactions. We found a catalyst system comprising a first catalyst that favors dealkylation over transalkylation reactions and a second catalyst that favors transalkylation over dealkylation reactions and the feedstock feeding to the first catalyst prior to the second catalyst. While not wishing to be bound by theory, we believe that transalkylation reactions take place via biphenylic-type transition states, and are favored in zeolitic catalysts having large channels, for example, in a 12 member-ring (12 MR) zeolites, e.g. mordenite, beta, ZSM-12, etc. Zeolites having 10 MR structures, for example ZSM-5 (MFI), tend to restrict the formation of this transition state necessary for transalkylation reactions, and therefore favor dealkylation reactions instead.

We, therefore, disclose a catalyst system for the transalkylation of $C_9+$ aromatics with $C_6$-$C_7$ aromatics. The catalyst system comprises (a) a first catalyst comprising a molecular sieve having a Constraint Index in the range of 3-12 (e.g., a 10 MR molecular sieve, such as ZSM-5, ZSM-11, ZSM-22, and ZSM-23) and a metal catalyzing the saturation of the olefins formed by the dealkylation reactions and (b) a second catalyst comprising a molecular sieve having a Constraint Index in the range of less than 3 (e.g., a 12 MR molecular sieve, such as ZSM-12, MOR, zeolite beta, MCM-22 family molecular sieve) and optionally a metal which may be the same or different to the metal on the first catalyst.

We also surprisingly discovered the catalyst system and a new process of using the catalyst system for transalkylation reactions comprising contacting a $C_9+$ feed with the first catalyst to form a product and then contacting at least a portion of the product with the second catalyst. This novel process allows for processing of heavy aromatic feed at high space velocities (high catalytic activity), which provides a significant advantage for a higher throughput transalkylation process. In addition, we surprisingly discovered that the use of this process and/or the catalyst system results in low aging rates for the catalyst system, thereby extending cycle lengths.

SUMMARY

In some embodiments, this disclosure relates to a process for producing xylene comprising:

a. contacting a $C_9+$ aromatic feedstock, hydrogen and a $C_6$-$C_7$ aromatic feedstock with a first catalyst comprising 0.01 to 5 wt. %, preferably 0.01 to 1 wt. %. of at least one source of a first metal element of Groups 6-10 and a first molecular sieve having a Constraint Index in the range of 3-12 under first conditions to form a first product, wherein the first conditions are selected such that the first product is substantially free of olefinic components and the first product contains at least 50 wt. % less ethyl-aromatic compounds and at least 70 wt. %, and preferably at least 75 wt. % less propyl-aromatic compounds than the $C_9+$ aromatic feedstock; then b. contacting at least a portion of the first product with a second catalyst comprising 0 to 5 wt. %, preferably 0.01 to 1 wt. %, of at least one source of a second metal element of Groups 6-10 and a second molecular sieve having a Constraint Index less than 3 under second conditions, wherein the second conditions are sufficient to transalkylate at least a portion of the $C_9+$ aromatic compounds in the $C_9+$ aromatic feedstock with at least a portion of the $C_6$-$C_7$ aromatic compounds in the $C_6$-$C_7$ aromatic feedstock to form a second product comprising xylene, wherein the second conditions are selected such that the second product is substantially free of olefinic components and a xylene yield in the range of 20 to 50 wt. %, and wherein the second product contains at least 60 wt. %, preferably at least 65 wt. %, and still more preferably 70 wt. % less ethyl-aromatic compounds and at least 80 wt. %, and preferably at least 85 wt. % less propyl-aromatic compounds than the $C_9+$ aromatic feedstock; and c. recovering the xylene.

In another embodiments, this disclosure relates to a process comprising:

a. contacting a $C_9+$ aromatic feedstock with a first catalyst comprising 0.01 to 5 wt. %, preferably 0.01 to 1 wt. %. of at least one source of a first metal element of Groups 6-10 and a first molecular sieve having a Constraint Index in the range of 3-12 under first conditions to form a first product, wherein the first conditions are selected such that the first product is substantially free of olefinic components and the first product contains at least 50 wt. % less ethyl-aromatic compounds and at least 75 wt. % less propyl-aromatic compounds than the $C_9+$ aromatic feedstock; then b. contacting at least a portion of the first product with a second catalyst comprising 0 to 5 wt. %, preferably 0.01 to 1 wt. %, of at least one source of a second metal element of Groups 6-10 and a second molecular sieve having a Constraint Index less than 3 under second conditions to form a second product, wherein the second conditions are selected such that the second product is substantially free of olefinic components and a xylene yield in the range of 20 to 50 wt. %, and wherein the second product contains at least 70 wt. % less ethyl-aromatic compounds and at least 85 wt. % less propyl-aromatic compounds than the $C_9+$ aromatic feedstock.

In other embodiments, this disclosure relates to an apparatus adapted for transalkylation of a $C_9+$ feedstock comprising:

a. a reactor containing a first catalyst having a first molecular sieve having a Constraint Index in the range of 3-12 and followed by a second catalyst having a second molecular sieve having a Constraint Index less than 3; and b. means for contacting a $C_9+$ feedstock and a $C_6$-$C_7$ feedstock to the first catalyst under first conditions and then to the second catalyst under second conditions.

In yet other embodiments, this disclosure relates to a catalyst system adapted for transalkylation of a $C_9+$ aromatic feedstock with a $C_6$-$C_7$ aromatic feedstock comprising:

a. a first catalyst comprising a first molecular sieve having 0.01 to 5 wt. %, preferably 0.01 to 1 wt. %. of at least one source of a first metal element of Groups 6-10 and a first molecular sieve having a Constraint Index in the range of 3-12; and b. a second catalyst comprising a second molecular sieve having 0 to 5 wt. %, preferably 0.01 to 1 wt. %, of at least one source of a second metal element of Groups 6-10 and a second molecular sieve having a Constraint Index less than 3, wherein the weight ratio of the first catalyst over the second catalyst is in the range of 5:95 to 75:25, preferably in the range of 20:80 and 50:50, and wherein the first catalyst is located in front of the second catalyst when they are brought into contacting with the $C_9+$ aromatic feedstock and the $C_6$-$C_7$ aromatic feedstock in the present of hydrogen.

In some aspects, the first molecular sieve comprises at least one of ZSM-5, ZSM-11, ZSM-22, ZSM-23, ZSM-35, and ZSM-48. In other aspects, the second molecular sieve comprises at least one of zeolite beta, zeolite Y, Ultrastable Y (USY), Dealuminized Y (Deal Y), mordenite, NU-87, ZSM-3, ZSM-4 (Mazzite), ZSM-12, ZSM-18, MCM-22, MCM-36, MCM-49, MCM-56, EMM-10, EMM-10-P and ZSM-20. In a preferred embodiment, the first molecular sieve is ZSM-5 and the second molecular sieve is ZSM-12.

In a preferred embodiment, the first metal element and the second metal element are at least one of Pt, Re, Ir, and Pd.

In another preferred embodiment, the weight ratio of the first catalyst over the second catalyst is in the range of 5:95 to 75:25, preferably in the range of 20:80 and 50:50.

In some embodiments, the process of this disclosure further comprises a step of adjusting the flowrate of the $C_9+$ aromatic feedstock and the flowrate of the $C_6$-$C_7$ aromatic feedstock so that the combined aromatic feedstock having a methyl to single aromatic ring molar ratio in the range between 0.5 to 4, preferably between 1.0 to 2.5.

In some aspects, the first conditions are selected such that the first product is substantially free of olefinic components and the first product contains at least 70 wt. % less ethyl-aromatic compounds and at least 85 wt. % less propyl-aromatic compounds than the $C_9+$ aromatic feedstock and wherein the second conditions are selected such that the second product is substantially free of olefinic components and the xylene yield is in the range of 25 to 40 wt. %, and wherein the second product contains at least 80 wt. % less ethyl-aromatic compounds and at least 95 wt. % less propyl-aromatic compounds than the at least a portion of the first product.

In other aspects, the first molecular sieve has an alpha value in the range of 100 to 1500, preferably in the range of 300 to 500.

In some embodiments, where the $C_9+$ aromatic feedstock and/or the $C_6$-$C_7$ aromatic feedstock contains paraffinic compounds, the process further comprises a step of contacting the paraffinic compounds in the $C_9+$ aromatic feedstock and/or the $C_6$-$C_7$ aromatic feedstock with a third catalyst comprising a third molecular sieve having a Constraint Index in the range of 3-12 under cracking conditions sufficient to crack at least 50 wt. % of the paraffinic compounds.

In some embodiments, where the second product contains paraffinic compounds, the process further comprises a step of contacting the paraffinic compounds in the second product with a fourth catalyst comprising a fourth molecular sieve having a Constraint Index in the range of 3-12 under cracking conditions sufficient to crack at least 50 wt. % of the paraffinic compounds in the second product.

In some aspects, the first conditions comprise a temperature in the range of 100 to 1000° C., a pressure in the range of 790 to 7000 kPa-a (kilo -Pascal absolute), a $H_2$:HC molar ratio in the range of 0.01 to 20, a WHSV in the range of 0.01 to 100 $hr^{-1}$, and wherein the second conditions comprise a temperature in the range of 100° C. to 1000° C., a pressure in the range of 790 to 7000 kPa-a, a $H_2$:HC molar ratio in the range of 0.01 to 20, a WHSV in the range of 0.01 to 100 $hr^{-1}$.

In other aspects, the first conditions and the second conditions are selected such that the total ring-loss of the process is in the range of 0 to 3 wt. %.

DETAILED DESCRIPTION OF THE EMBODIMENTS

The present disclosure provides a process for converting a feed comprising $C_9+$ aromatic hydrocarbons, hydrogen, and $C_6$-$C_7$ aromatic hydrocarbons to produce a product containing xylenes. The process involves contacting a $C_9+$ aromatic feedstock, hydrogen and a $C_6$-$C_7$ aromatic feedstock with a first catalyst comprising a first molecular sieve having a Constraint Index in the range of 3-12 and 0.01 to 5 wt. %, preferably 0.01 to 1 wt. %, of a first metal element of Groups 6-10 under first conditions to form a first product, wherein the first conditions are selected such that the first product is substantially free of olefinic components and the first product contains at least 50 wt. % less ethyl-aromatic compounds and at least 75 wt. % less propyl-aromatic compounds than the $C_9+$ aromatic feedstock and then contacting at least a portion of the first product with a second catalyst comprising a second molecular sieve having a Constraint Index less than 3 and 0 to 5 wt. %, preferably 0.01 to 1 wt. %, of a second metal element of Groups 6-10 under second conditions, wherein the second conditions are sufficient to transalkylate at least a portion of the $C_9+$ aromatic compounds in the $C_9+$ aromatic feedstock with at least a portion of the $C_6$-$C_7$ aromatic compounds in the $C_6$-$C_7$ aromatic feedstock to form a second product comprising the xylenes, wherein the second conditions are selected such that the second product is substantially free of olefinic components and a xylene yield in the range of 20 to 50 wt. %, and wherein the second product contains at least 70 wt. % less ethyl-aromatic compounds and at least 85 wt. % less propyl-aromatic compounds than the at least a portion of the first product.

As used in this specification, the term "framework type" is used in the sense described in the "Atlas of Zeolite Framework Types," 2001.

As used herein, the numbering scheme for the Periodic Table Groups is used as in Chemical and Engineering News, 63(5), 27 (1985).

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system. Materials belong to the MCM-22 family include MCM-22 (described in U.S. Pat. No. 4,954,325 and U.S. patent application Ser. No. 11/823,722), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575), UZM-8 (described in U.S. Pat. No. 6,756,030), MCM-56 (described in U.S. Pat. No. 5,362,697), EMM-10-P (described in U.S. patent application Ser. No. 11/823,129), and EMM-10 (described in U.S. patent application Ser. Nos. 11/824,742 and 11/827,953). The entire contents of the patents are incorporated herein by reference.

The term "wppm" as used herein is defined as parts per million by weight.

As used herein, the term "substantially free" means less than 1 wt. %, preferably less than 0.1 wt. %. For example, that a product is substantially free of olefinic components means the product has less than 1 wt. %, preferably less than 0.1 wt. % olefinic components based on the total weight of the product.

The xylene yield, as used herein, is calculated by dividing the total weight of the xylene isomers (para-, meta-, and ortho-xylene) by the total weight of the product stream. The total weight of the xylene isomers can be calculated by multiplying the weight percentage of the xylene isomers, as determined by gas chromatography, by the total weight of the product stream.

The ring-loss, as used herein, is calculated by the following formula:

Ring loss(%)=(1−total moles of aromatic compounds in product/total moles of aromatic compounds in feed)*100

The methyl over aromatic ring ratio is calculated by dividing the total moles of methyl group attaching to an aromatic ring in an aromatic feedstock over the total moles of single aromatic ring in the same aromatic feedstock.

The term "ethyl-aromatic compounds" means aromatic compounds having an ethyl group attached to the aromatic ring. The term "propyl-aromatic compounds" means aromatic compounds having a propyl group attached to the aromatic ring.

The ethyl content of the $C_9$+ aromatic feedstock is calculated by multiplying the molecular weight of $C_2H_5$ by the total mole fraction of aromatics having an ethyl group, where single ethyl substituted aromatics, e.g. 1,4-ethyltoluene are counted once, and di-substituted aromatic rings, e.g. 1,2-diethylbenzene, are counted twice.

The propyl content of the $C_9$+ aromatic feedstock is calculated by multiplying the molecular weight of $C_3H_7$ by the total mole fraction of aromatics having a propyl group, where single propyl substituted aromatics, e.g. n-propylbenzene are counted once, and di-substituted aromatic rings, e.g. 1,4-dipropylbenzene, are counted twice.

Weight of molecular sieve, weight of binder, weight of catalyst composition, weight ratio of molecular sieve over catalyst composition, weight ratio of the first catalyst over the second catalyst and weight ratio of binder over catalyst composition are calculated based on calcined weight (at 510° C. in air for 24 hours), i.e., the weight of the molecular sieve, the binder, and the catalyst composition are calculated based on the weight of the molecular sieve, the binder, and the catalyst composition after being calcined at 510° C. in air for twenty-four hours.

The term "aromatic" as used herein is to be understood in accordance with its art-recognized scope which includes alkyl substituted and unsubstituted mono- and polynuclear compounds.

The term "$C_n$" hydrocarbon wherein n is an positive integer, e.g., 1, 2, 3, 4, 5, 6, 7, 8, 9, 10, 11, 12, as used herein means a hydrocarbon having n number of carbon atom(s) per molecular. For example, $C_n$ aromatics means an aromatic hydrocarbon having n number of carbon atom(s) per molecular. The term "$C_n$+" hydrocarbon wherein n is an positive integer, e.g., 1, 2, 3, 4, 5, 6, 7, 8, 9, 10, 11, 12, as used herein means a hydrocarbon having at least n number of carbon atom(s) per molecular. The term "$C_n$−" hydrocarbon wherein n is an positive integer, e.g., 1, 2, 3, 4, 5, 6, 7, 8, 9, 10, 11, 12, as used herein means a hydrocarbon having no more than n number of carbon atom(s) per molecular.

The term "$C_n$ feedstock", wherein n is a positive integer, e.g., 1, 2, 3, 4, 5, 6, 7, 8, 9, 10, 11, 12, as used herein, means that the $C_n$ feedstock comprises greater than 50 wt. % of hydrocarbons having n number of carbon atom(s) per molecule. The term "$C_n$+ feedstock", wherein n is a positive integer, e.g., 1, 2, 3, 4, 5, 6, 7, 8, 9, 10, 11, 12, as used herein, means that the $C_n$+ feedstock comprises greater than 50 wt. % of hydrocarbons having at least n number of carbon atom(s) per molecule. The term "$C_n$− feedstock" wherein n is a positive integer, e.g., 1, 2, 3, 4, 5, 6, 7, 8, 9, 10, 11, 12, as used herein, means that the $C_n$− feedstock comprises greater than 50 wt. % of hydrocarbons having no more than n number of carbon atom(s) per molecule. The term "$C_n$ aromatic feedstock", wherein n is a positive integer, e.g., 1, 2, 3, 4, 5, 6, 7, 8, 9, 10, 11, 12, as used herein, means that the $C_n$ aromatic feedstock comprises greater than 50 wt. % of aromatic hydrocarbons having n number of carbon atom(s) per molecule. The term "$C_n$+ aromatic feedstock", wherein n is a positive integer, e.g., 1, 2, 3, 4, 5, 6, 7, 8, 9, 10, 11, 12, as used herein, means that the $C_n$+ aromatic feedstock comprises greater than 50 wt. % of aromatic hydrocarbons having at least n number of carbon atom(s) per molecule. The term "$C_n$− aromatic feedstock" wherein n is a positive integer, e.g., 1, 2, 3, 4, 5, 6, 7, 8, 9, 10, 11, 12, as used herein, means that the $C_n$− aromatic feedstock comprises greater than 50 wt. % of aromatic hydrocarbons having no more than n number of carbon atom(s) per molecule.

Catalyst Composition

The catalyst composition used in the process of the disclosure comprises:

a. a first catalyst comprising a first molecular sieve having 0.01 to 5 wt. % of at least one source of a first metal element of Groups 6-10 and a Constraint Index in the range of 3-12; and b. a second catalyst comprising a second molecular sieve having 0 to 5 wt. % of at least one source of a second metal element of Groups 6-10 and a Constraint Index less than 3 and, wherein the weight ratio of the first catalyst over the second catalyst is in the range of 5:95 to 75:25 and wherein the first catalyst is located in front of the second catalyst when they are brought into contacting with the $C_9+$ aromatic feedstock and the $C_6$-$C_7$ aromatic feedstock in the present of hydrogen.

The Constraint Index is a convenient measure of the extent to which an aluminosilicate or molecular sieve provides controlled access to molecules of varying sizes to its internal structure. For example, aluminosilicates which provide a highly restricted access to and egress from its internal structure have a high value for the constraint index, and aluminosilicates of this kind usually have pores of small size, e.g. less than 5 Angstroms. On the other hand, aluminosilicates which provide relatively free access to the internal aluminosilicate structure have a low value for the constraint index, and usually pores of large size. The method by which constraint index is determined is described fully in U.S. Pat. No. 4,016,218, which is incorporated herein by reference for the details of the method.

A molecular sieve having a Constraint Index of 3-12 (as defined in U.S. Pat. No. 4,016,218), includes ZSM-5, ZSM-11, ZSM-22, ZSM-23, ZSM-35, ZSM-48, ZSM-57 and ZSM-58. ZSM-5 is described in detail in U.S. Pat. No. 3,702,886 and Re. 29,948. ZSM-11 is described in detail in U.S. Pat. No. 3,709,979. ZSM-22 is described in U.S. Pat. Nos. 4,556,477 and 5,336,478. ZSM-23 is described in U.S. Pat. No. 4,076,842. ZSM-35 is described in U.S. Pat. No. 4,016,245. ZSM-48 is more particularly described in U.S. Pat. Nos. 4,234,231 and 4,375,573. ZSM-57 is described in U.S. Pat. No. 4,873,067. ZSM-58 is described in U.S. Pat. No. 4,698,217. The entire contents of all the above patent specifications are incorporated herein by reference.

A molecular sieve having a Constraint Index of less than 3 (as defined in U.S. Pat. No. 4,016,218), includes zeolite beta, zeolite Y, Ultrastable Y (USY), Dealuminized Y (Deal Y), mordenite, ZSM-3, ZSM-4, ZSM-12, ZSM-18, NU-87 and ZSM-20. Zeolite ZSM-4 is described in U.S. Pat. No. 3,923,636. Zeolite ZSM-12 is described in U.S. Pat. No. 3,832,449. Zeolite ZSM-20 is described in U.S. Pat. No. 3,972,983. Zeolite Beta is described in U.S. Pat. No. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Rare earth exchanged Y (REY) is described in U.S. Pat. No. 3,524,820. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104. The entire contents of all the above patent specifications are incorporated herein by reference.

In one embodiment, the first molecular sieve is a ten member ring molecular sieve and the second molecular sieve is a twelve member ring molecular sieve. Examples of ten member ring molecular sieve are ZSM-5, ZSM-11, ZSM-22, ZSM-23, ZSM-35, ZSM-48, ZSM-57 and ZSM-58. Examples of twelve member ring molecular sieve are zeolite beta, zeolite Y, Ultrastable Y (USY), Dealuminized Y (Deal Y), mordenite, ZSM-3, ZSM-4, ZSM-12, ZSM-18, NU-87 and ZSM-20.

With regard to the molecular sieve having a Constraint Index of less than 3, ZSM-12 is more particularly described in U.S. Pat. No. 3,832,449. Mordenite occurs naturally but may also be used in one of its synthetic forms, such as TEA-mordenite (i.e., synthetic mordenite prepared from a reaction mixture comprising a tetraethylammonium directing agent), which is disclosed in U.S. Pat. Nos. 3,766,093 and 3,894,104. Examples of suitable porous crystalline inorganic oxide materials having the defined X-ray diffraction pattern include MCM-22, PSH-3, SSZ-25, MCM-36, MCM-49 or MCM-56. MCM-22 is described in U.S. Pat. No. 4,954,325, PSH-3 is described in U.S. Pat. No. 4,439,409, SSZ-25 is described in U.S. Pat. No. 4,826,667, MCM-36 is described in U.S. Pat. No. 5,250,277, MCM-49 is described in U.S. Pat. No. 5,236,575 and MCM-56 is described in U.S. Pat. No. 5,362,697. The entire contents of each of the aforementioned patents are incorporated herein by reference.

Typically, the first catalyst comprises at least 1 wt. %, preferably at least 10 wt. %, more preferably at least 50 wt. %, and most preferably at least 65 wt. %, of the first molecular sieve. The second catalyst comprises at least 1 wt. %, preferably at least 10 wt. %, more preferably at least 50 wt. %, and most preferably at least 65 wt. %, of the second molecular sieve.

The catalyst system has a weight ratio of the first catalyst over the second catalyst in the range of 5:95 to 75:25, preferably in the range of 10:90 to 60:40, and more preferably in the range of 20:80 to 50:50.

In some embodiments, the first molecular sieve has an Alpha value of at least 150, such as at least 300. In other embodiments, the first molecular sieve has an Alpha value in the range of 100-1500, preferably in the range of 300-600.

Where the first molecular sieve is ZSM-5, the ZSM-5 can have a composition involving the molar $YO_2$ over $X_2O_3$=n, wherein X is a trivalent element, such as aluminum, boron, iron, indium and/or gallium, preferably aluminum; Y is a tetravalent element, such as silicon, tin and/or germanium, preferably silicon; and n is less than 1000, such as from 10 to less than 100. The ZSM-5 may further be selected so as to have an average crystal size of less than 0.1 micron, such as about 0.05 micron, and a Diffusion Parameter, $D/r^2$, for mesitylene of at least $1000 \times 10^{-6}$ $sec^{-1}$, such as at least $2000 \times 10^{-6}$ $sec^{-1}$, when measured at a temperature of 100° C. and a mesitylene pressure of 2 torr.

In a preferred embodiment, the first molecular sieve is ZSM-5 and the second molecular sieve is ZSM-12.

Where the second molecular sieve is ZSM-12, the ZSM-12 can have a composition involving the molar $YO_2$ over $X_2O_3$=n, wherein X is a trivalent element, such as aluminum, boron, iron, indium and/or gallium, preferably aluminum; Y is a tetravalent element, such as silicon, tin and/or germanium, preferably silicon; and n is less than 500, such as from 50 to less than 300. The ZSM-12 may further be selected so as to have an average crystal size of less than 0.1 micron, such as about 0.05 micron, and a Diffusion Parameter, $D/r^2$, for mesitylene of at least $1000 \times 10^{-6}$ sec$^{-1}$, such as at least $2000 \times 10^{-6}$ sec$^{-1}$, when measured at a temperature of 100° C. and a mesitylene pressure of 2 torr.

As used herein, the Diffusion Parameter of a particular porous crystalline material is defined as $D/r^2 \times 10^6$, wherein D is the diffusion coefficient (cm$^2$/sec) and r is the crystal radius (cm). The required diffusion parameters can be derived from sorption measurements provided the assumption is made that the plane sheet model describes the diffusion process. Thus for a given sorbate loading Q, the value $Q/Q_\infty$, where $Q_\infty$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

In some embodiments, the second molecular sieve has an Alpha value of at least 20, such as at least 30. In other embodiments, the second molecular sieve has an Alpha value in the range of 20-500, preferably in the range of 20-100, alternatively in the range of 40-100 or 30-100.

The alpha value test is a measure of the cracking activity of a catalyst and is described in U.S. Pat. No. 3,354,078 and in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

It may be desirable to incorporate each molecular sieve in the catalyst composition with another material that is resistant to the temperatures and other conditions employed in the transalkylation process of the disclosure. Such materials include active and inactive materials and synthetic or naturally occurring zeolites, as well as inorganic materials such as clays, silica and/or metal oxides such as alumina. The inorganic material may be either naturally occurring, or in the form of gelatinous precipitates or gels including mixtures of silica and metal oxides.

Use of a material in conjunction with each molecular sieve, i.e. combined therewith or present during its synthesis, which itself is catalytically active, may change the conversion and/or selectivity of the catalyst composition. Inactive materials suitably serve as diluents to control the amount of conversion so that transalkylated products can be obtained in an economical and orderly manner without employing other means for controlling the rate of reaction. These catalytically active or inactive materials may be incorporated into, for example, naturally occurring clays, e.g. bentonite and kaolin, to improve the crush strength of the catalyst composition under commercial operating conditions. It is desirable to provide a catalyst composition having good crush strength because in commercial use, it is desirable to prevent the catalyst composition from breaking down into powder-like materials.

Naturally occurring clays that can be composited with each molecular sieve as a binder for the catalyst composition include the montmorillonite and kaolin family, which families include the subbentonites, and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, each molecular sieve can be composited with a porous matrix binder material, such as an inorganic oxide selected from the group consisting of silica, alumina, zirconia, titania, thoria, beryllia, magnesia, and combinations thereof, such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. It may also be advantageous to provide at least a part of the foregoing porous matrix binder material in colloidal form so as to facilitate extrusion of the catalyst composition.

Each molecular sieve is usually admixed with the binder or matrix material so that the final catalyst composition contains the binder or matrix material in an amount ranging from 5 to 95 wt. %, and typically from 10 to 60 wt. %.

The first catalyst comprises 0.01 to 5 wt. %, preferably 0.1 to 2 wt. %, more preferably 0.1 to 1 wt. %, of a first metal element of Groups 6-10. The second catalyst comprises 0 to 5 wt. %, preferably 0.01 to 2 wt. %, more preferably 0.01 to 1 wt. %, of a second metal element of Groups 6-10. The first metal element and the second metal element may be at least one hydrogenation component, such as tungsten, vanadium, molybdenum, rhenium, chromium, manganese, a metal selected from Groups 6-10 of the Periodic Table of the Elements, or mixtures thereof. Specific examples of useful metals are iron, ruthenium, osmium, nickel, cobalt, rhodium, iridium, and noble metals such as platinum or palladium. Preferably, the hydrogenation component is palladium, platinum or rhenium.

The amount of the hydrogenation component is selected according to a balance between hydrogenation activity and catalytic functionality. Less of the hydrogenation component is required when the most active metals such as platinum are used as compared to palladium, which does not possess such strong hydrogenation activity. Generally, the catalyst composition contains less than 5 wt. % of the hydrogenation component and typically from 0.01 wt. % to 2 wt. % of the component.

The hydrogenation component can be incorporated into the catalyst composition by co-crystallization, exchanged into the composition to the extent a Group 13 element, e.g., aluminum, is in the molecular sieve structure, impregnated therein, or mixed with the molecular sieve and binder. Such component can be impregnated in or on the molecular sieve, for example in the case of platinum, by treating the molecular sieve with a solution containing a platinum metal-containing ion. Suitable platinum compounds for impregnating the catalyst with platinum include chloroplatinic acid, platinous chloride and various compounds containing the platinum amine complex, such as $Pt(NH_3)_4Cl_2 \cdot H_2O$.

Alternatively, a compound of the hydrogenation component may be added to the molecular sieve when it is being composited with a binder, or after the molecular sieve and binder have been formed into particles by extrusion or pelletizing.

After treatment with the hydrogenation component, the molecular sieve is usually dried by heating at a temperature of 65° C. to 160° C., typically 110° C. to 143° C., for at least 1 minute and generally not longer than 24 hours, at pressures ranging from 100 to 200 kPa-a. Thereafter, the molecular sieve may be calcined in a stream of dry gas, such as air or nitrogen, at temperatures of from 260° C. to 650° C. for 1 to 20 hours. Calcination is typically conducted at pressures ranging from 100 to 300 kPa-a.

Prior to use, steam treatment of the catalyst composition may be employed to minimize the aromatic hydrogenation activity of the catalyst composition. In the steaming process, the catalyst composition is usually contacted with from 5 to 100% steam, at a temperature of at least 260° to 650° C. for at least one hour, specifically 1 to 20 hours, at a pressure of 100 to 2590 kPa-a.

In addition, prior to contacting the catalyst composition with the hydrocarbon feed, the hydrogenation component can be sulfided. This is conveniently accomplished by contacting the catalyst with a source of sulfur, such as hydrogen sulfide, at a temperature ranging from about 320 to 480° C. The source of sulfur can be contacted with the catalyst via a carrier gas, such as hydrogen or nitrogen. Sulfiding per se is known and sulfiding of the hydrogenation component can be accomplished without more than routine experimentation by one of ordinary skill in the art in possession of the present disclosure.

Apparatus

In some embodiments, this disclosure relates to apparatus adapted for transalkylation a $C_9+$ feedstock comprising:
  a. a reactor containing a first catalyst having a first molecular sieve having a Constraint Index in the range of 3-12 and followed by a second catalyst having a second molecular sieve having a Constraint Index less than 3; and
  b. means for contacting a $C_9+$ feedstock and a $C_6$-$C_7$ feedstock to the first catalyst under first conditions and then to the second catalyst under second conditions.

In one aspect, the first conditions are the same as the second conditions. In another aspect, the first catalyst is loaded in a first reaction zone of the reactor and the second catalyst is loaded in a second reaction zone of the reactor.

In other embodiments, this disclosure relates to apparatus adapted for transalkylation a $C_9+$ feedstock comprising:
  a. a first reactor containing a first catalyst having a first molecular sieve having a Constraint Index in the range of 3-12 and followed by a second reactor containing a second catalyst having a second molecular sieve having a Constraint Index less than 3; and
  b. means for contacting a $C_9+$ feedstock and a $C_6$-$C_7$ feedstock to the first catalyst under first conditions and then to the second catalyst under second conditions.

In the apparatus of the disclosure, the first and second catalysts may be loaded in a same reactor, or may be loaded in two separate reactors. In all situations, the first catalyst is not mixed with the second catalyst and the hydrocarbon feedstocks and hydrogen are contacting with the first catalyst prior to contacting the second catalyst. In some embodiments, the first catalyst may be separated from the second catalyst by space or by inert materials, such as, alumina balls or sand. The means for contacting a $C_9+$ feedstock and a $C_6$-$C_7$ feedstock to the first catalyst under first conditions and then to the second catalyst under second conditions include:
  (a) load the first catalyst on the top of the second catalyst when the hydrocarbon feedstocks are flowing top-down;
  (b) load the second catalyst on the top of the first catalyst when the hydrocarbon feedstocks are flowing bottom-up;
  (c) load the first catalyst in the inner part of the reactor and the second catalyst outside of the first catalyst loading when the hydrocarbon feedstocks are flowing inside-out; or
  (d) load the second catalyst in the inner part of the reactor and the first catalyst outside of the second catalyst loading when the hydrocarbon feedstocks are flowing from outside to inside.

Means for contacting a $C_9+$ feedstock and a $C_6$-$C_7$ feedstock to the first catalyst under first conditions and then to the second catalyst under second conditions include pipe arrangement, control valves, flow meters, pumps, or any combination thereof. Other means for contacting a $C_9+$ feedstock and a $C_6$-$C_7$ feedstock to the first catalyst under first conditions and then to the second catalyst under second conditions include pumping or supplying the $C_9+$ feedstock and $C_6$-$C_7$ feedstock to the catalyst and followed by pumping or supplying the product of the first contacting step to the second catalyst.

Feedstock

The aromatic feed used in the process of the disclosure comprises one or more aromatic compounds containing at least 9 carbon atoms. Specific $C_9+$ aromatic compounds found in a typical feed include mesitylene (1,3,5-trimethylbenzene), durene (1,2,4,5-tetramethylbenzene), hemimellitene (1,2,4-trimethylbenzene), pseudocumene (1,2,4-trimethylbenzene), 1,2-methylethylbenzene, 1,3-methylethylbenzene, 1,4-methylethylbenzene, propyl-substituted benzenes, butyl-substituted benzenes, and dimethylethylbenzenes. Suitable sources of the $C_9+$ aromatics are any $C_9+$ fraction from any refinery process that is rich in aromatics. This aromatics fraction contains a substantial proportion of $C_9+$ aromatics, e.g., at least 80 wt. % $C_9+$ aromatics, wherein preferably at least 80 wt. %, and more preferably more than 90 wt. %, of the hydrocarbons will range from $C_9$ to $C_{12}$. Typical refinery fractions which may be useful include catalytic reformate, FCC naphtha or TCC naphtha.

The feed to the process of the disclosure also includes benzene or toluene. In one practical embodiment, the feed to the transalkylation reactor comprises $C_9+$ aromatics hydrocarbons and toluene. The feed may also include recycled/unreacted toluene and $C_9+$ aromatic feedstock that is obtained by distillation of the effluent product of the transalkylation reaction itself. Typically, toluene constitutes from 0 to 90 wt. %, such as from 10 to 70 wt. % of the entire feed, whereas the $C_9+$ aromatics component constitutes from 10 to 100 wt. %, such as from 30 to 85 wt. % of the entire feed to the transalkylation reaction.

The feedstock may be characterized by the methyl over single aromatic ring molar ratio. In some embodiments, the combined feedstock (the combination of the $C_9+$ and the $C_6$-$C_7$ aromatic feedstocks) has a methyl over single aromatic ring molar ratio in the range of from 0.5 to 4, preferably from 1 to 2.5, more preferably from 1.5 to 2.25. The methyl over single aromatic ring molar ratio may be adjusted by adjusting relative flowrate of the $C_9+$ and the $C_6$-$C_7$ aromatic feedstocks and/or the relative $C_6/C_7$ ratio of the $C_6$-$C_7$ aromatic feedstock.

Hydrocarbon Conversion Process

In some embodiments, this disclosure relates to a process for producing xylene comprising:
  a. contacting a $C_9+$ aromatic feedstock, hydrogen and a $C_6$-$C_7$ aromatic feedstock with a first catalyst comprising 0.01 to 5 wt. %, preferably 0.01 to 1 wt. %, of at least one source of a first metal element of Groups 6-10 and a first molecular sieve having a Constraint Index in the range of 3-12 under first conditions to form a first product, wherein the first conditions are selected such that the first product is substantially free of olefinic components and the first product contains at least 50 wt. % less ethyl-aromatic compounds and at least 75 wt. % less propyl-aromatic compounds than the $C_9+$ aromatic feedstock; then
  b. contacting at least a portion of the first product with a second catalyst comprising 0 to 5 wt. %, preferably 0.01 to 1 wt. %, of at least one source of a second metal element of Groups 6-10 and a second molecular sieve having a Constraint Index less than 3 under second conditions, wherein the second conditions are sufficient to transalkylate at least a portion of the $C_9+$ aromatic compounds in the $C_9+$ aromatic feedstock with at least a portion of the $C_6$-$C_7$ aromatic compounds in the $C_6$-$C_7$ aromatic feedstock to form a second product comprising xylene, wherein the second conditions are selected such that the second product is substantially free of olefinic components and the xylene yield is in the range of 20 to 50 wt. %, and wherein the second product contains at least 60 wt. %, preferably at least 65 wt. %, still more preferably at least 70 wt. % less ethyl-aromatic compounds and at least 70 wt. %, preferably at lest 75 wt. %, still more preferably at least 85 wt. % less propyl-aromatic compounds than the $C_9$+ aromatic feedstock; and c. recovering the xylene.

In another embodiments, this disclosure relates to a process comprising:

a. contacting a $C_9$+ aromatic feedstock with a first catalyst comprising 0.01 to 5 wt. %, preferably 0.01 to 1 wt. %. of at least one source of a first metal element of Groups 6-10 and a first molecular sieve having a Constraint Index in the range of 3-12 under first conditions to form a first product, wherein the first conditions are selected such that the first product is substantially free of olefinic components and the first product contains at least 50 wt. % less ethyl-aromatic compounds and at least 75 wt. % less propyl-aromatic compounds than the $C_9$+ aromatic feedstock; then b. contacting at least a portion of the first product with a second catalyst comprising 0 to 5 wt. %, preferably 0.01 to 1 wt. %, of at least one source of a second metal element of Groups 6-10 and a second molecular sieve having a Constraint Index less than 3 under second conditions to form a second product, wherein the second conditions are selected such that the second product is substantially free of olefinic components and the xylene yield is in the range of 20 to 50 wt. %, and wherein the second product contains at least 60 wt. %, preferably at least 65 wt. %, still more preferably at least 70 wt. % less ethyl-aromatic compounds and at least 70 wt. %, preferably at lest 75 wt. %, still more preferably at least 85 wt. % less propyl-aromatic compounds than the $C_9$+ aromatic feedstock.

The process can be conducted in any appropriate reactor including a radial flow, fixed bed, continuous down flow or fluid bed reactor. The first conditions and/or the second conditions comprise a temperature in the range of 100 to 1000° C., preferably in the range of 300 to 500° C.; a pressure in the range of 790 to 7000 kPa-a (kilo-Pascal absolute), preferably in the range of 2170 to 3000 kPa-a, a $H_2$:HC molar ratio in the range of 0.01 to 20, preferably in the range of 1-10; a WHSV in the range of 0.01 to 100 $hr^{-1}$, preferably in the range of 1-20. The second conditions comprise a temperature in the range of 100 to 1000° C., a pressure in the range of 790 to 7000 kPa-a, a $H_2$:HC molar ratio in the range of 0.01 to 20, a WHSV in the range of 0.01 to 100 $hr^{-1}$.

The first and/or the second conditions may be same. The first and the second conditions are sufficient to convert the heavy aromatic feed to a product containing more xylene than the combined feedstock.

In some embodiments, the first conditions are selected such that the first product is substantially free of olefinic components and the first product contains at least 50 wt. % less, preferably at least 70 wt. % less, ethyl-aromatic compounds and at least 75 wt. % less, preferably at least 85 wt. % less, propyl-aromatic compounds than the $C_9$+ aromatic feedstock.

In other embodiments, the second conditions are sufficient to transalkylate at least a portion of the $C_9$+ aromatic compounds in the $C_9$+ aromatic feedstock with at least a portion of the $C_6$-$C_7$ aromatic compounds in the $C_6$-$C_7$ aromatic feedstock to form a second product comprising xylene, wherein the second conditions are selected such that the second product is substantially free of olefinic components and the xylene yield is in the range of 20 to 50 wt. %, and wherein the second product contains at least 70 wt. % less, preferably at least 80 wt. % less, ethyl-aromatic compounds and at least 85 wt. % less, preferably at least 95 wt. % less, propyl-aromatic compounds than the at least a portion of the first product.

In some embodiments, where the $C_9$+ aromatic feedstock and/or the $C_6$-$C_7$ aromatic feedstock contains paraffinic compounds, the process further comprises a step of contacting the paraffinic compounds in the $C_9$+ aromatic feedstock and/or the $C_6$-$C_7$ aromatic feedstock with a third catalyst comprising a third molecular sieve having a Constraint Index in the range of 3-12 under first cracking conditions sufficient to crack at least 50 wt. % of the paraffinic compounds.

In some embodiments, where the second product contains paraffinic compounds, the process further comprises a step of contacting the paraffinic compounds in the second product with a fourth catalyst comprising a fourth molecular sieve having a Constraint Index in the range of 3-12 under second cracking conditions sufficient to crack at least 50 wt. % of the paraffinic compounds in the second product.

The first cracking conditions and/or the second cracking conditions comprise a temperature in the range of 100 to 1000° C., preferably in the range of 300 to 500° C.; a pressure in the range of 790 to 7000 kPa-a (kilo-Pascal absolute), preferably in the range of 2170 to 3000 kPa-a, a $H_2$:HC molar ratio in the range of 0.01 to 20, preferably in the range of 1-10; a WHSV in the range of 0.01 to 100 $hr^{-1}$, preferably in the range of 1-20. The second conditions comprise a temperature in the range of 100° C. to 1000° C., a pressure in the range of 790 to 7000 kPa-a, preferably in the range of 2170 to 3000 kPa-a; a $H_2$:HC molar ratio in the range of 0.01 to 20, a WHSV in the range of 0.01 to 100 $hr^{-1}$.

In other aspects, the first conditions and the second conditions are selected such that the total ring-loss of the process is in the range of 0 to 3 wt. %, preferably in the range of 0.5-1.5 wt. %.

The disclosure will now be more particularly described with reference to the following Examples.

EXAMPLES

Comparative Example 1

A ZSM-5 zeolite having a Si/$Al_2$ ratio of ~87 and crystal dimensions of 2-4 μm was formulated into a 1/20" quadrilobe extrudate using Versal 300 alumina such that the mass ratio of zeolite crystal to alumina was 1:1. This extrudate was converted into the acidic form by exchanging with $NH_4NO_3$, followed by calcination, and then steamed to moderate the catalyst activity to an alpha value of about 450. 0.5% Rhenium was then added to the catalyst via incipient wetness techniques known to those skilled in the art. This catalyst was then tested in a fixed-bed microunit. The reactor pressure was 350 psig and the $H_2$:HC ratio was 2:1. The feed to the reactor contained 85% heavy aromatics and 15% benzene+toluene. A detailed analysis of the feed is shown in Table 1. The catalyst was reduced in hydrogen for 1 hour at 400° C. and 2500 kPa-a prior to the introduction of feed. The activity of the catalyst was determined as a function of reactor temperature spanning the range from 380 to 420° C. The total feed flowrate, expressed as grams feed per gram catalyst per hour (WHSV) was 10 $hr^{-1}$. Product analysis occurred using on-line GC-FID with a 60 m DB-WAX column. Separate off-line analyses of the light gas produced occurred using a GC-FID with a 60 m DB-1 column.

TABLE 1

| Feed Composition | % |
|---|---|
| C5– gas | 0.00 |
| Benzene | 8.55 |
| Toluene | 6.39 |
| Ethylbenzene | 0.00 |
| Xylenes | 0.21 |
| EthylToluene | 22.93 |
| Trimethylbenzene | 39.09 |
| Propylbenzene | 2.65 |
| 1,n-ethylxylene | 10.56 |
| Tetramethylbenzene | 2.45 |
| Other C10 aromatic | 5.31 |
| Other C11 aromatic | 0.30 |
| Other C12 aromatic | 0.00 |
| Indanes | 0.74 |
| Alkylindanes | 0.00 |
| Napthalene | 0.01 |
| Alkylnaphthalene | 0.00 |
| Heavies | 0.00 |
| Unidentified | 0.80 |

The analysis of the performance of the catalyst for dealkylation of heavy aromatics at 420° C. is shown in Table 2.

Comparative Example 2

A ZSM-5 zeolite having a $Si/Al_2$ ratio of ~57 and crystal dimensions of ~0.05-0.1 μm was formulated into a 1/16" cylindrical extrudate using Versal 300 alumina such that the mass ratio of zeolite crystal to alumina was 1.86:1. This extrudate was converted into the acidic form by exchanging with $NH_4NO_3$, followed by calcination, and then steamed to a catalyst activity, as measured by the alpha test, that was similar to the catalyst in Comparative Example 1. 0.5% Rhenium was then added to the catalyst via incipient wetness techniques known to those skilled in the art. This catalyst was then tested in a fixed-bed microunit in the same manner as the catalyst in Comparative Example 1. The analysis of the performance of this catalyst for dealkylation of heavy aromatics at 420° C. is shown in Table 2.

Comparative Example 3

A ZSM-5 zeolite having a $Si/Al_2$ ratio of ~56 and crystal dimensions of 1-2 μm was formulated into a 1/16" cylindrical extrudate using Versal 300 alumina such that the mass ratio of zeolite crystal to alumina was 1.86:1. This extrudate was converted into the acidic form by exchanging with $NH_4NO_3$, followed by calcination, and then steamed to a catalyst activity, as measured by the alpha test, that was similar to the catalyst in Comparative Example 1. 0.5% Rhenium was then added to the catalyst via incipient wetness techniques known to those skilled in the art. This catalyst was then tested in a fixed-bed microunit in the same manner as the catalyst in Comparative Example 1. The analysis of the performance of this catalyst for dealkylation of heavy aromatics at 420° C. is shown in Table 2.

TABLE 2

| | Example 1 | Example 2 | Example 3 |
|---|---|---|---|
| Total Xylenes | 5.3 | 14.5 | 9.8 |
| EthylBenzene | 2.7 | 2.6 | 2.3 |

TABLE 2-continued

| | Example 1 | Example 2 | Example 3 |
|---|---|---|---|
| PX/Total Xyl | 25.9% | 24.2% | 24.6% |
| PX Purity | 17.1% | 21.5% | 19.9% |
| Benzene Conversion | −8.0% | −7.0% | −8.8% |
| Toluene Conversion | −192.7% | −228.2% | −212.9% |
| Ethyltoluene Conversion | 76.2% | 87.9% | 81.8% |
| Ethylxylene Conversion | 13.9% | 63.4% | 31.2% |
| 1,3,5 TMB Conversion | −7.0% | −6.8% | −4.7% |
| 1,2,4 TMB Conversion | 5.4% | 24.9% | 19.8% |
| 1,2,3 TMB Conversion | 2.5% | 26.5% | 7.1% |
| C9 Conversion | 34.4% | 48.2% | 42.8% |
| C10 Conversion | 38.3% | 60.5% | 48.7% |
| C9/C10 Conversion | 35.2% | 50.8% | 44.0% |
| Tol + C9/C10 Conversion | 17.2% | 28.6% | 23.7% |
| Total TMBs | 36.43 | 30.36 | 32.39 |
| Total TeMBs | 2.27 | 2.69 | 2.26 |
| Total C11+ | 2.18 | 2.62 | 3.00 |
| % De-Ethylation | 59.2% | 82.7% | 68.0% |
| % De-Propylation | 94.0% | 98.6% | 96.1% |
| Total Saturates | 0.00 | 0.02 | 0.00 |
| Light Gas | 6.2 | 8.2 | 7.5 |

Analysis of the performance of the catalysts shows that these catalysts are very effective for dealkylating the feed. Conversion of ethyltoluenes varies from 76.2% to 87.9% at 420° C., and generally increases with decreasing crystal size of the ZSM-5. Overall de-ethylation rates, including ethyltoluene, ethylxylene and diethyl aromatics varied from 59.2% to 82.7% at 420° C. Depropylation rates, of predominately cumene and n-propylbenzene, were 94.0% for the larger crystals and 98.6% for the smaller crystals. Production of heavy components, e.g. alkylindanes, naphthalenes, alkylnaphthalenes, etc, was low. These data illustrate the suitability of this catalyst for dealkylating the heavy aromatics feed. This dealkylated feed is now more suitable for transalkylation reactions in a second catalyst bed as the $C_9+:C_7+C_6$ ratio has been decreased.

Comparative Example 4

A ZSM-5 zeolite having a $Si/Al_2$ ratio of ~56 and crystal dimensions of ~0.05-0.1 μm was formulated into a 1/20" quadrilobe extrudate using Versal 300 alumina such that the mass ratio of zeolite crystal to alumina was 1.86:1. This extrudate was converted into the acidic form by exchanging with $NH_4NO_3$, followed by calcination, and then steamed to a catalyst activity, as measured by the alpha test, that was similar to the catalyst in Comparative Example 1. 0.075 wt. % Platinum was then added to the catalyst via incipient wetness techniques known to those skilled in the art. This catalyst was then tested in a fixed-bed microunit in the same manner as the catalyst in Comparative Example 1. The analysis of the performance of this catalyst for dealkylation of heavy aromatics at 420° C. is shown in Table 3.

Comparative Example 5

A ZSM-5 zeolite having a $Si/Al_2$ ratio of ~56 and crystal dimensions of ~0.05-0.1 μm was formulated into a 1/20" quadrilobe extrudate using Versal 300 alumina such that the mass ratio of zeolite crystal to alumina was 1.86:1. This extrudate was converted into the acidic form by exchanging with $NH_4NO_3$, followed by calcination, and then steamed to a catalyst activity, as measured by the alpha test, that was similar to the catalyst in Comparative Example 1. 0.075 wt. % Platinum and 0.3 wt. % Rhenium were then added to the catalyst via incipient wetness techniques known to those skilled in the art. This catalyst was then tested in a fixed-bed microunit in the same manner as the catalyst in Comparative Example 1. The analysis of the performance of this catalyst for dealkylation of heavy aromatics at 420° C. is shown in Table 3.

Comparative Example 6

A ZSM-5 zeolite having a $Si/Al_2$ ratio of ~56 and crystal dimensions of ~0.05-0.1 µm was formulated into a 1/16" cylindrical extrudate using Versal 300 alumina such that the mass ratio of zeolite crystal to alumina was 1.86:1. About 0.115 wt. % Platinum was added to the catalyst during preparation. This extrudate was converted into the acidic form by exchanging with $NH_4NO_3$, followed by calcination, and then steamed to a catalyst activity, as measured by the alpha test, that was similar to the catalyst in Comparative Example 1. This catalyst was then tested in a fixed-bed microunit in the same manner as the catalyst in Comparative Example 1. The analysis of the performance of this catalyst for dealkylation of heavy aromatics at 420° C. is shown in Table 3.

Comparative Example 7

A ZSM-5 zeolite having a $Si/Al_2$ ratio of ~56 and crystal dimensions of ~0.05-0.1 µm was formulated into a 1/20" quadrilobe extrudate using Versal 300 alumina such that the mass ratio of zeolite crystal to alumina was 1:1. This extrudate was converted into the acidic form by exchanging with $NH_4NO_3$, followed by calcination, and then steamed to a catalyst activity, as measured by the alpha test, that was similar to the catalyst in Comparative Example 1. 0.075% Platinum was then added to the catalyst via incipient wetness techniques known to those skilled in the art. This catalyst was then tested in a fixed-bed microunit in the same manner as the catalyst in Comparative Example 1. The analysis of the performance of this catalyst for dealkylation of heavy aromatics at 420° C. is shown in Table 3.

TABLE 3

| | Example 4 | Example 5 | Example 6 | Example 7 |
|---|---|---|---|---|
| Total Xylenes | 14.1 | 13.2 | 13.7 | 12.8 |
| EthylBenzene | 0.5 | 0.7 | 0.3 | 1.1 |
| PX/Total Xyl | 24.1% | 24.2% | 24.1% | 24.2% |
| PX Purity | 23.3% | 23.0% | 23.5% | 22.3% |
| Benzene Conversion | −0.3% | −6.0% | −3.0% | −1.6% |
| Toluene Conversion | −222.8% | −226.3% | −221.9% | −218.9% |
| Ethyltoluene Conversion | 96.2% | 95.3% | 97.7% | 92.6% |
| Ethylxylene Conversion | 61.1% | 57.2% | 70.8% | 53.3% |
| 1,3,5 TMB Conversion | −11.2% | −12.0% | −14.2% | −8.3% |
| 1,2,4 TMB Conversion | 18.5% | 16.6% | 14.9% | 18.8% |
| 1,2,3 TMB Conversion | 18.0% | 17.2% | 20.7% | 14.8% |
| C9 Conversion | 47.6% | 46.4% | 46.5% | 46.5% |
| C10 Conversion | 64.4% | 61.5% | 68.2% | 59.9% |
| C9/C10 Conversion | 51.1% | 49.5% | 51.1% | 49.3% |
| Tol + C9/C10 Conversion | 29.4% | 27.7% | 29.4% | 28.0% |
| Total TMBs | 32.71 | 33.27 | 33.71 | 32.55 |
| Total TeMBs | 2.59 | 2.73 | 2.80 | 2.63 |
| Total C11+ | 2.59 | 2.73 | 2.88 | 3.04 |
| % De-Ethylation | 86.6% | 84.9% | 90.3% | 81.9% |
| % De-Propylation | 99.3% | 99.1% | 99.1% | 98.9% |
| Total Saturates | 0.32 | 0.14 | 0.10 | 0.15 |
| Light Gas | 10.7 | 9.2 | 13.7 | 9.6 |

Analysis of the performance of these catalysts show that they are very effective at dealkylating the heavy aromatic feed. Overall de-ethylation rates with these catalysts vary from 81.9% to 90.3%, and overall de-propylation rates vary from 98.9% to 99.3%. While not wishing to be bound by theory, it is believed that a high olefin saturation activity of the metal enhances the overall dealkylation activity as the olefins are saturated before having the opportunity to re-alkylate onto an aromatic ring. However, if the metal activity is too high, then aromatic ring saturation can occur and ring losses can increase.

Comparative Example 8

A ZSM-12 zeolite having a $Si/Al_2$ ratio of ~200 and crystal dimensions of ~0.1 µm was formulated into a 1/16" cylindrical extrudate using Versal 300 alumina such that the mass ratio of zeolite crystal to alumina was 1.86:1. About 0.1 wt. % Platinum was added to the catalyst during preparation. This extrudate was converted into the acidic form by exchanging with $NH_4NO_3$, followed by calcination, and then steamed to moderate the catalyst activity. This catalyst was then tested in a fixed-bed microunit. The reactor pressure was 2514 kPa-a and the $H_2$:HC ratio was 2:1. The feed to the reactor contained 85 wt. % $C_9$+ and 15 wt. % benzene+toluene. A detailed analysis of the feed is shown in Table 1. The catalyst was initially reduced in hydrogen at 427° C. and 350 psig, then sulfided with 5 moles of $H_{2S}$ per mole of platinum on the catalyst prior to the introduction of feed. The reactor temperature was set to maintain an overall $C_9+C_{10}$ conversion of ~57.5±0.5 wt. %. The total feed flowrate, expressed as grams feed per gram catalyst per hour (WHSV) was 3 $hr^{-1}$. Product analysis (see Table 4) occurred using on-line GC-FID with a 60 m DB-WAX column.

TABLE 4

| Day-on-Stream (start) | 12.0 |
|---|---|
| Average RX T (° F.) | 783 |
| De-ethylation (%) | 65.4 |
| De-propylation (%) | 99.4 |
| Conversion (%) | |
| Benzene | 49.9 |
| C9 | 60.9 |
| C10 | 48.3 |
| C9 + C10 | 58.1 |
| Toluene + C9 + C10 | 41.5 |
| Yields (wt. %) | |
| Light Gas (C5−) | 7.2 |
| Benzene | 4.3 |
| Toluene | 17.6 |
| Ethylbenzene | 2.8 |
| Xylenes | 25.8 |
| C9 Aromatics | 25.3 |
| C10 Aromatics | 9.5 |
| C11+ Aromatics | 5.9 |
| TMB | 17.5 |
| TetraMB | 3.3 |
| Naphthalenes | 0.4 |
| AlkylNaphthalenes | 1.4 |

The aging rate, expressed as the increase in temperature required to maintain constant conversion was 6.2° C. per month for this catalyst. As the data in Table 4 shows, the single bed system produces a significant amount of heavier components, specifically $C_{11}$+ aromatics.

Example 1

The transalkylation of heavy aromatics with benzene and toluene was demonstrated over the dual bed catalyst system of this disclosure in a fixed-bed microunit. The top bed was a 1/20" quadrilobe 50:50 ZSM-5:$Al_2O_3$ extrudate that had been impregnated with 0.5 wt. % Re, the same catalyst tested in Comparative Example 1. The bottom bed was a 1/16" cylindrical 65:35 ZSM-12:Al$_2$O$_3$ extrudate containing 0.1 wt. % Pt, as used in Comparative Example 8. The ratio of the top bed to the bottom bed was 3:7. The reactor pressure was 2514 kPa-a and the H$_2$:HC ratio was 2:1. The feed to the reactor contained 85 wt. % C$_9$+ aromatic feedstock and 15 wt. % benzene+toluene. A detailed analysis of the feed is shown in Table 1. The reactor temperature was varied between 412° C. and 432°, and the weight hourly space velocity (WHSV) was varied between 2.8 and 4 hr$^{-1}$. On start-up, the catalyst beds were reduced in hydrogen at 420° C. and 350 psig, and then sulfided with 5 moles of H$_2$S per mole of platinum and rhenium on the catalyst prior to introducing feed. After feed was introduced, the catalyst beds were de-edged by running with a H$_2$:HC ratio of 1 for the first 48 hours. Product analysis (see table 5) occurred using on-line GC-FID with a 60 m DB-WAX column.

TABLE 5

| | |
|---|---|
| Day-on-Stream (start) | 10.0 |
| Average RX T (° F.) | 791 |
| De-ethylation (%) | 72.5 |
| De-propylation (%) | 100.0 |
| Conversion (%) | |
| Benzene | 42.7 |
| C9 | 61.1 |
| C10 | 54.7 |
| C9 + C10 | 59.7 |
| Toluene + C9 + C10 | 40.9 |
| Yields (wt. %) | |
| Light Gas (C5−) | 7.9 |
| Benzene | 4.9 |
| Toluene | 19.4 |
| Ethylbenzene | 2.3 |
| Xylenes | 28.3 |
| C9 Aromatics | 25.1 |
| C10 Aromatics | 8.3 |
| C11+ Aromatics | 3.0 |
| TMB | 19.0 |
| TetraMB | 3.5 |
| Naphthalenes | 0.2 |
| AlkylNaphthalenes | 0.6 |

As the data in Table 5 indicates, the dual bed catalyst system has higher overall dealkylation rates despite the fact that a higher space velocity is being used. In addition, the amount of heavy components, specifically C$_{11}$+ aromatics, is down by almost a factor of 2. As a result, the aging rate, expressed as the increase in temperature required to maintain constant conversion was 1.6° C. per month for this catalyst, a significant improvement over the single bed comparative example.

As has been indicated by this disclosure, the use of a dual bed system for heavy aromatics transalkylation provides significant benefits over existing technologies. The dual bed system allows for processing of heavier feeds, and for processing feeds at higher throughput through the reactor, thereby increasing production. In addition, the low aging rate of this dual bed system allows for longer catalyst cycles, and the reduced down-time resulting from reduced catalyst change-outs or catalyst regenerations leads to significant monetary savings.

Although numerous embodiments are detailed above and yet even more embodiments would be readily apparent to one of ordinary skill in the art in possession of the present disclosure, some particularly preferred embodiments may be pointed out as follows: a process for producing xylene comprising: (a) contacting a C$_9$+ aromatic feedstock, hydrogen and a C$_6$-C$_7$ aromatic feedstock with a first catalyst comprising 0.01 to 5 wt. % of at least one source of a first metal element of Groups 6-10 and a first molecular sieve having a Constraint Index in a range of 3-12 under first conditions to form a first product, wherein said first conditions are selected such that said first product is substantially free of olefinic components and said first product contains at least 50 wt. % less ethyl-aromatic compounds and at least 75 wt. % less propyl-aromatic compounds than the C$_9$+ aromatic feedstock; then (b) contacting at least a portion of said first product with a second catalyst comprising 0 to 5 wt. % of at least one source of a second metal element of Groups 6-10 and a second molecular sieve having a Constraint Index less than 3 under second conditions, wherein said second conditions are sufficient to transalkylate at least a portion of the C$_9$+ aromatic compounds in said C$_9$+ aromatic feedstock with at least a portion of the C$_6$-C$_7$ aromatic compounds in said C$_6$-C$_7$ aromatic feedstock to form a second product comprising xylene, wherein said second conditions are selected such that said second product is substantially free of olefinic components and a xylene yield is in the range of 20 to 50 wt. %, and wherein said second product contains at least 60 wt. %, preferably at least 65 wt. %, still more preferably at least 70 wt. % less ethyl-aromatic compounds and at least 70 wt. %, preferably at least 75 wt %, still more preferably at least 85 wt. % less propyl-aromatic compounds than the C$_9$+ aromatic feedstock; and (c) recovering said xylene; and more particularly at least one of the following more preferred embodiments, which may be combined as would be apparent to one of ordinary skill in the art in possession of the present disclosure, to wit: the process wherein said first molecular sieve comprises at least one of ZSM-5, ZSM-11, ZSM-22, ZSM-23, ZSM-35, and ZSM-48; and/or wherein said second molecular sieve comprises at least one of zeolite beta, zeolite Y, Ultrastable Y (USY), Dealuminized Y (Deal Y), mordenite, NU-87, ZSM-3, ZSM-4 (Mazzite), ZSM-12, ZSM-18, MCM-22, MCM-36, MCM -49, MCM-56, EMM-10, EMM-10-P and ZSM-20; and/or wherein the weight ratio of said first catalyst over said second catalyst is in the range of 5:95 to 75:25; and/or further comprising a step of adjusting the flowrate of said C$_9$+ aromatic feedstock and the flowrate of said C$_6$-C$_7$ aromatic feedstock so that the combined aromatic feedstock having a methyl to single aromatic ring molar ratio in the range between 0.5 to 4, preferably 1.0 to 3.0; and/or wherein said first molecular sieve has an alpha value in the range of 100 to 1500; and/or wherein said second molecular sieve has an alpha value in the range of 20 to 500; and/or wherein said first metal element and said second metal element are at least one of Pt, Pd, Ir and Re; and/or wherein said second product contains paraffinic compounds, said process further comprises a step of contacting said paraffinic compounds in said second product with a third catalyst comprising a third molecular sieve having a Constraint Index in the range of 3-12 under cracking conditions sufficient to crack at least 50 wt. % of said paraffinic compounds in said second product; and/or wherein said first conditions comprise a temperature in the range of 100° C. to 1000° C., a pressure in the range of 790-7000 kPa-a, a H$_2$:HC molar ratio in the range of 0.01 to 20, a WHSV in the range of 0.01 to 100 hr$^{-1}$, and wherein said second conditions comprise a temperature in the range of 100° C. to 1000° C., a pressure in the range of 790-7000 kPa-a, a H$_2$:HC molar ratio in the range of 0.01 to 20, a WHSV in the range of 0.01 to 100 hr$^{-1}$; and/or wherein said first conditions and said second conditions are selected such that the total ring -loss of the process is in the range of 0 to 3 wt. %; and/or wherein said first molecular sieve is ZSM-5 and said second molecular sieve is ZSM-12; and/or wherein ZSM-5 has a particle size of less 1 micron, and said ZSM-12 has a particle size of less than 0.5 micron. Yet another preferred embodiment is a catalyst system adapted for transalkylation a C$_9$+ aromatic feedstock with a C$_6$-C$_7$ aromatic feedstock comprising: (a) a first catalyst comprising a first molecular sieve having a Constraint Index in the range of 3-12 and 0.01 to 5 wt. % of at least one source of a first metal element of Groups 6-10; and (b) a second catalyst comprising a second molecular sieve having a Constraint Index less than 3 and 0 to 5 wt. % of at least one source of a second metal element of Groups 6-10, wherein the weight ratio of said first catalyst over said second catalyst is in the range of 5:95 to 75:25 and wherein said first catalyst is located in front of said second catalyst when they are brought into contacting with said $C_9$+ aromatic feedstock and said $C_6$-$C_7$ aromatic feedstock in the present of hydrogen; which may likewise be modified by yet still more preferable embodiments which may be combined as would be apparent to one of ordinary skill in the art in possession of the present disclosure, to wit: wherein said first molecular sieve comprises at least one of ZSM-5, ZSM-11, ZSM-22, ZSM-23, ZSM-35, and ZSM-48, and said second molecular sieve comprises at least one of zeolite beta, zeolite Y, Ultrastable Y (USY), Dealuminized Y (Deal Y), mordenite, NU-87, ZSM-3, ZSM-4 (Mazzite), ZSM-12, ZSM-18, MCM-22, MCM-36, MCM-49, MCM-56, EMM-10, EMM-10-P and ZSM-20; and/or wherein said first catalyst comprises 0.01 to 1 wt. % said first metal element, and said second catalyst comprises 0.01 to 1 wt. % said second metal element; and/or wherein said first metal element and said second metal element are Pt; and/or wherein said first molecular sieve is ZSM-5 and said second molecular sieve is ZSM-12, particularly the case wherein said ZSM-5 has a particle size of less 1 micron, and said ZSM-12 has a particle size of less than 0.5 micron. Also contemplated is the process or catalyst system as set forth in this specification and particularly the process or catalyst system specified in this paragraph including a step of sulfiding at least one of said first and said second catalysts prior to said contacting step.

The meanings of terms used herein shall take their ordinary meaning in the art; reference shall be taken, in particular, to Handbook of Petroleum Refining Processes, Third Edition, Robert A. Meyers, Editor, McGraw-Hill (2004). In addition, all patents and patent applications, test procedures (such as ASTM methods), and other documents cited herein are fully incorporated by reference to the extent such disclosure is not inconsistent with this invention and for all jurisdictions in which such incorporation is permitted. Also, when numerical lower limits and numerical upper limits are listed herein, ranges from any lower limit to any upper limit are contemplated. Note further that Trade Names used herein are indicated by a ™ symbol or ® symbol, indicating that the names may be protected by certain trademark rights, e.g., they may be registered trademarks in various jurisdictions.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The invention claimed is:

1. A process for producing xylene comprising:
    a. contacting a $C_9$+ aromatic feedstock, hydrogen and a $C_6$-$C_7$ aromatic feedstock with a first catalyst comprising 0.01 to 5 wt. % of at least one source of a first metal element of Groups 6-10 and a first molecular sieve having a Constraint Index in a range of 3-12 under first conditions to form a first product, wherein said first conditions are selected such that said first product is substantially free of olefinic components and said first product contains at least 50 wt. % less ethyl-aromatic compounds and at least 75 wt. % less propyl-aromatic compounds than the $C_9$+ aromatic feedstock; then
    b. contacting at least a portion of said first product with a second catalyst comprising 0 to 5 wt. % of at least one source of a second metal element of Groups 6-10 and a second molecular sieve having a Constraint Index less than 3 under second conditions, wherein said second conditions are sufficient to transalkylate at least a portion of the $C_9$+ aromatic compounds in said $C_9$+ aromatic feedstock with at least a portion of the $C_6$-$C_7$ aromatic compounds in said $C_6$-$C_7$ aromatic feedstock to form a second product comprising xylene, wherein said second conditions are selected such that said second product is substantially free of olefinic components and a xylene yield is in the range of 20 to 50 wt. %, and wherein said second product contains at least 60 wt. % less ethyl-aromatic compounds and at least 70 wt. % less propyl-aromatic compounds than the $C_9$+ aromatic feedstock; and
    c. recovering said xylene.

2. The process of claim 1, wherein said first molecular sieve comprises at least one of ZSM-5, ZSM-11, ZSM-22, ZSM-23, ZSM-35, and ZSM-48.

3. The process of claim 1, wherein said second molecular sieve comprises at least one of zeolite beta, zeolite Y, Ultrastable Y (USY), Dealuminized Y (Deal Y), mordenite, NU-87, ZSM-3, ZSM-4 (Mazzite), ZSM-12, ZSM-18, MCM-22, MCM-36, MCM-49, MCM-56, EMM-10, EMM-10-P and ZSM-20.

4. The process of claim 1, wherein the weight ratio of said first catalyst over said second catalyst is in the range of 5:95 to 75:25.

5. The process of claim 1, further comprising a step of adjusting the flowrate of said $C_9$+ aromatic feedstock and the flowrate of said $C_6$-$C_7$ aromatic feedstock so that the combined aromatic feedstock having a methyl to single aromatic ring molar ratio in the range between 0.5 to 4.

6. The process of claim 1, wherein said first molecular sieve has an alpha value in the range of 100 to 1500.

7. The process of claim 1, wherein said second molecular sieve has an alpha value in the range of 20 to 500.

8. The process of claim 1, wherein said first metal element and said second metal element are at least one of Pt, Pd, Ir and Re.

9. The process of claim 1, wherein said first conditions comprise a temperature in the range of 100° C. to 1000° C., a pressure in the range of 790-7000 kPa-a, a $H_2$:HC molar ratio in the range of 0.01 to 20, a WHSV in the range of 0.01 to 100 $hr^{-1}$, and wherein said second conditions comprise a temperature in the range of 100° C. to 1000° C., a pressure in the range of 790-7000 kPa-a, a $H_2$:HC molar ratio in the range of 0.01 to 20, a WHSV in the range of 0.01 to 100 $hr^{-1}$.

10. The process of claim 1, wherein said first conditions and said second conditions are selected such that the total ring-loss of the process is in the range of 0 to 3 wt. %.

11. The process of claim 1, wherein said first molecular sieve is ZSM-5 and said second molecular sieve is ZSM-12.

12. The process of claim 11, wherein said ZSM-5 has a particle size of less 1 micron, and said ZSM-12 has a particle size of less than 0.5 micron.

13. The process of claim 1, including a step of sulfiding at least one of said first and said second catalysts prior to said contacting step.

* * * * *